United States Patent [19]

Minikane

[11] Patent Number: 4,534,651
[45] Date of Patent: Aug. 13, 1985

[54] PHOTOMETRIC BIOCHEMICAL ANALYZER

[75] Inventor: Tomiharu Minikane, Ohtawara, Japan

[73] Assignee: Kabushiki Kaisha Toshiba, Japan

[21] Appl. No.: 594,993

[22] Filed: Mar. 29, 1984

[30] Foreign Application Priority Data

Mar. 29, 1983 [JP] Japan ................. 58-54674

[51] Int. Cl.³ ............................ G01N 21/00
[52] U.S. Cl. ................... 356/440; 250/576; 350/590; 356/244; 356/409; 356/436; 422/64; 422/65

[58] Field of Search ............. 356/440, 436, 409, 244; 250/576; 422/64, 65; 350/590

Primary Examiner—Bernard D. Pianalto
Attorney, Agent, or Firm—Finnegan, Henderson, Farabow, Garrett & Dunner

[57] ABSTRACT

In accordance with the present invention, apparatus for photometric light absorption measurements of liquid samples contained in reaction cuvettes comprises a temperature controlled bath unit in which at least one light path conversion means is immersed in the fluid bath medium and is provided with at least two layers, one light-reflective layer and one non-corrosive layer on a surface thereof.

8 Claims, 6 Drawing Figures

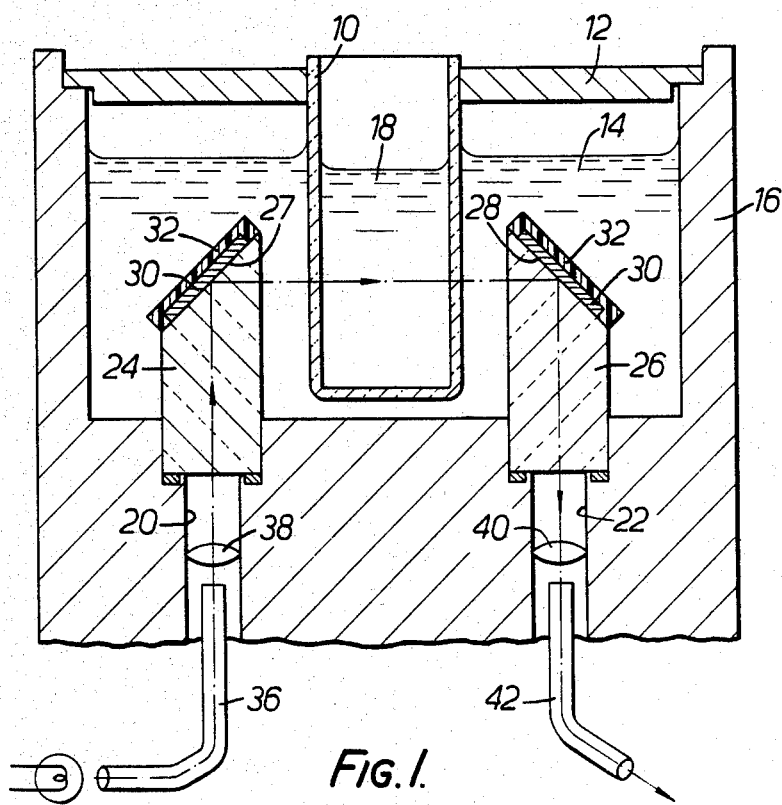
FIG. 1.
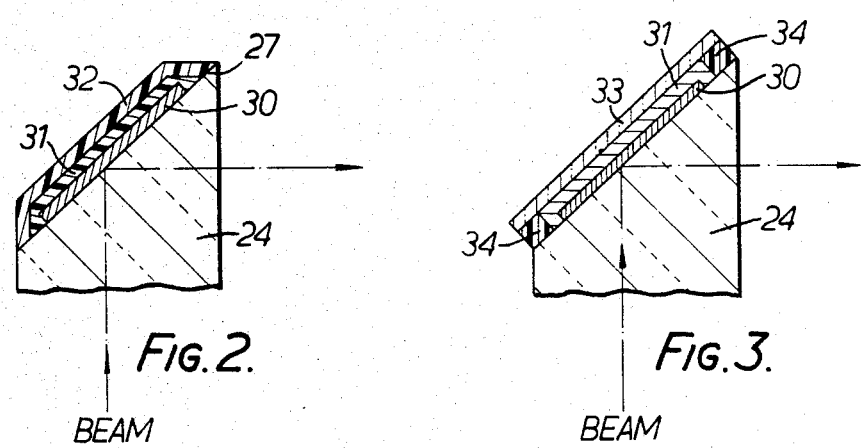
FIG. 2.  FIG. 3.
BEAM  BEAM

PHOTOMETRIC BIOCHEMICAL ANALYZER

BACKGROUND OF THE INVENTION

This invention relates to a photometric light absorption type biochemical analyzing apparatus and in particular to an improved analyzer apparatus having a highly flexible light path arrangement.

Photometric light absorption measurements are normally made by directing a light beam through a transparent reaction cuvette containing a liquid sample to be analyzed and by detecting the intensity of the light transmitted through the sample.

An automatic biochemical analyzing apparatus of this type usually includes a temperature controlled bath unit for keeping the reaction cuvette at a predetermined temperature. The conventional temperature control unit is constructed so that a single line of successive sample cuvettes immersed in the water of the bath unit, moves across the path of the beam, which also propagates through the bath fluid.

Specifically, the light beam emitted from a light source is directed to the reaction curvettes within the bath unit through an entrance window provided on a side wall of the bath unit and the portion of the light beam transmitted through the sample is directed through an exit window provided on the opposite side wall of the bath unit. The transmitted light is then separated into spectrum components for determining the concentration of the sample.

In such a conventional apparatus, light path conversion means, such as prisms, are disposed outside the bath unit with the bath unit interposed therebetween.

One reason for this arrangement is that it is difficult to obtain sufficient transmitted light intensities when the prism means are directly immersed in the water of the bath unit due to the small differences of the indices of refraction of the prism and the water. One approach that has been considered is the provision of reflexible metal on the reflection surface of the prism. However, this has led to problems of corrosion of the metal coating because a surface-active agent is usually added to the temperature controlled water for preventing attachment of bubbles to the surfaces of the reaction cuvettes. The addition of antifreeze agents also contributes to these difficulties.

As a consequence, in the conventional apparatus the prism means are usually positioned outside of the bath unit adjacent to the side wall windows.

In such a conventional apparatus, it is difficult, if not impossible, to measure simultaneously a plurality of cuvette sample lines running parallel between the side wall windows of the temperature controlled bath unit. Further, it is difficult to devise a compact arrangement for simultaneously measuring plural samples moving in parallel paths through the fluid bath.

OBJECTS OF THE INVENTION

It is accordingly an object of this invention to provide a new and improved photometric light absorption measuring type biochemical analyzing apparatus.

Another object of this invention is to provide improve apparatus which is adapted for use with a biochemical analyzer and which can obtain sufficient transmitted light intensities through a fluid bath medium.

A further object of this invention is to provide improved light measurement apparatus which can be configured to set up a plurality of different light paths in the temperature controlled bath unit.

A still further object of this invention is to provide new and improved light absorption measuring apparatus having light path conversion means immersed in the fluid bath medium.

A still further object of the invention is to provide a new and improved apparatus for photometric light absorption measuring type biochemical analysis which performs simultaneous measurements of plural sample lines immersed in a temperature controlled fluid medium.

A still further object of the invention is to provide an improved new apparatus for performing photometric light measurements with high speed and high reliability.

BRIEF DESCRIPTION OF THE DRAWINGS

The above and other objects and significant advantages of this invention are made clear by the following detailed description thereof taken in conjunction with the accompanying drawings wherein:

FIG. 1 is a sectional view of the light measuring section of a first embodiment incorporating the present invention.

FIGS. 2 and 3 are partly sectioned views of another embodiment of light path conversion means usable in the system of the invention.

Referring now to FIG. 1, a plurality of reaction cuvettes 10 (only the front cuvette is shown) are supported on a moving cassette 12 so as to move through temperature controlled liquid 14, such as water, contained in a temperature controlled bath unit 16. Each cassette 10 contains a liquid sample 18 to be analyzed and is partly immersed in the water 14 for maintaining the sample 18 at a predetermined reaction temperature.

Figure 4:
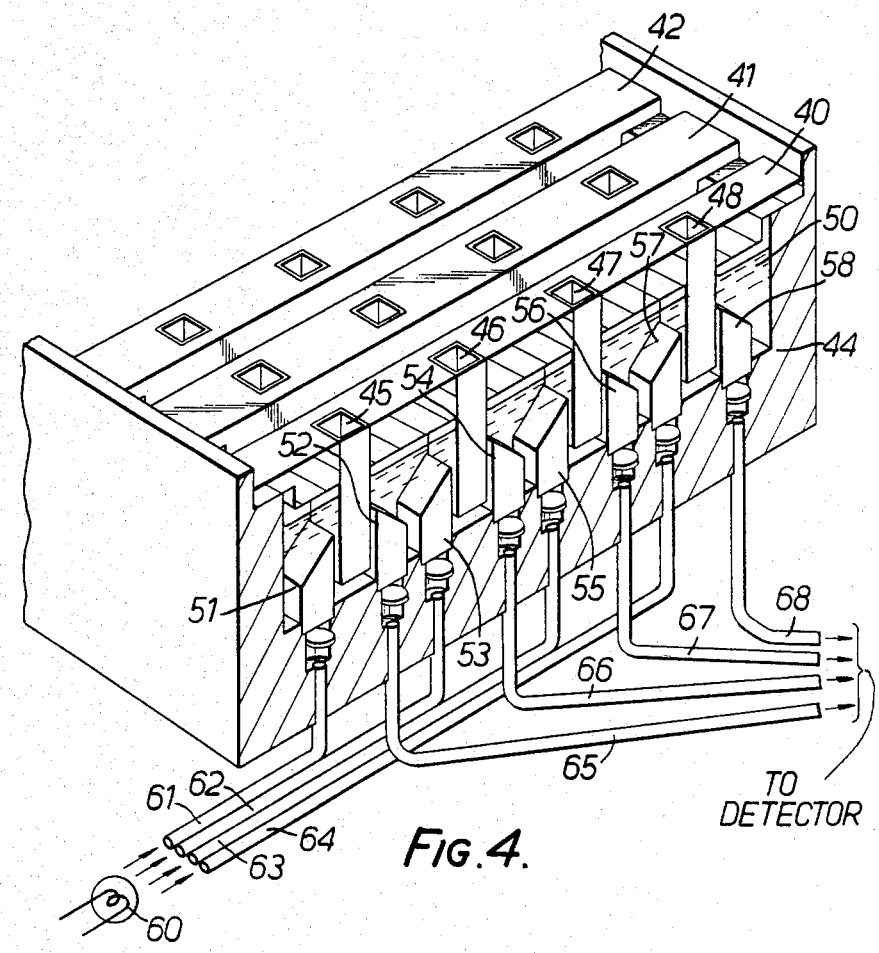
FIG. 4 is a perspective view, partially sectioned, of an apparatus employing the elements of FIG. 1 for simultaneously measuring a plurality of samples.

The support cassette 12 is intermittently moved so as to bring each sample cuvette 10 to a light intensity measuring station which is provided at a predetermined position or plurality of positions within the bath unit. The measuring station includes at least a pair of windows 20 and 22 provided in the bottom portion of the unit 16. Light path conversion means 24 and 26, such as light reflecting mirrors or prisms, are provided at each window opening. The respective light path conversion planes 27 and 28 of the respective prisms 24 and 26 are oriented to define a light inspection path therebetween and through the cuvette 10.

The respective light path conversion means 24 and 26 include a prism body and at least two layers 30 and 32 coated on the respective light path conversion planes 27 and 28 thereof. The first layer 30 of light reflective material may be, for example, aluminum (Al) and the second layer 32 may be of a non-corrosive material, i.e., a chemically resistant material such as titanium (Ti), chlorine (Cl), or silicon (Si). The oxide forms of the above materials are preferable, such as titanium dioxide ($TiO_2$), silicon oxide (SiO) or silicon dioxide ($SiO_2$).

Since the chemically resistant layer 32 covers the first layer 30, no corrosion of the reflective aluminum layer occurs even when the prism means are immersed in water in which a surface-active agent has been added. Consequently, the light transmission efficiency of the conversion means does not deteriorate over time.

The light beam emitted from a light source 34 is guided to the light entrance window 20 of the bath unit 16 by an optical fiber 36 and is directed to the first prism 24 through a focusing lens 38. The light beam is reflected approximately 90° by the first prism 24 so as to irradiate the sample cuvette 10 passing between the prisms. After passing through sample 18, the light beam is reflected again approximately 90° by the second prism 26 provided at exit window 22 of the bath unit 16.

Optical fiber 42 directs the transmitted light beam to a detector means (not shown) after it traverses a focusing lens 40.

By this construction, the prisms 24 and 26 can be immersed into the water without losing light transmission efficiency. Accordingly, the apparatus can be made compact since the windows can be located at the bottom portion of the bath unit.

FIGS. 2 and 3 show other embodiments of the prism structures. In FIG. 2, a light reflective thin layer 120, such as aluminum (Al) is deposited on a light path conversion plane 122 of the prism body 24. Moreover, double thin layers 126 and 128 of different chemically resistant materials are deposited to cover the aluminum layer 120. For example, the layer 126 may be of chlorine (Cl) and the top layer 128 may be of titanium (Ti). The chlorine acts as a buffer layer to prevent direct chemical reaction between the aluminum and the titanium.

FIG. 3 depicts another embodiment of the non-corrosive structure of the prism. On the aluminum layer 120 a non-corrosive material 130 is coated, and further a thin glass plate 132 is fixed over them by an expoxy adhesive 134.

According to this invention, it is possible to construct an apparatus which can perform simultaneous measurement of plural samples. FIG. 4 shows an embodiment of such an apparatus. Successive cassette holders 40, 41 and 42, for example, intermittently run along a temperature controlled bath unit 44. Each cassette holds a plurality of sample cuvettes 45, 46, 47 and 48 which contain samples to be analyzed. The cuvettes are partially immersed in the water 50 contained in the bath unit 44.

A plurality of prism pairs are provided at light measuring stations in the bath unit. In this embodiment, four pairs of prisms are provided for simultaneously measuring four samples. Specifically, four pairs of prisms 51 and 52, 53 and 54, 55 and 56, and 57 and 58 are respectively positioned so as to define four light measuring paths.

Light beams emitted from a light source 60 are directed through a plurality of optical guides 61, 62, 63 and 64 which are connected to the respective light entrance windows provided at the bottom portion of the bath unit 44 and irradiate simultaneously the prisms 51, 53, 55 and 57 through the respective focusing lenses.

The light beams are reflected by the respective light path conversion surfaces of the prisms in order to simultaneously irradiate the sample cuvettes 45, 46, 47 and 48. The transmitted beams are respectively directed out the respective light exit windows by the respective prisms 52, 54, 56 and 58. Further, the transmitted beams are directed to absorption detector means (not shown) through a plurality of optical guides 65, 66, 67 and 68.

Each prism is, of course, constructed as shown in FIGS. 1, 2 or 3. As is apparent from this figure, the simultaneous measurement of plural samples is achieved in an extremely compact apparatus.

Figure 5:
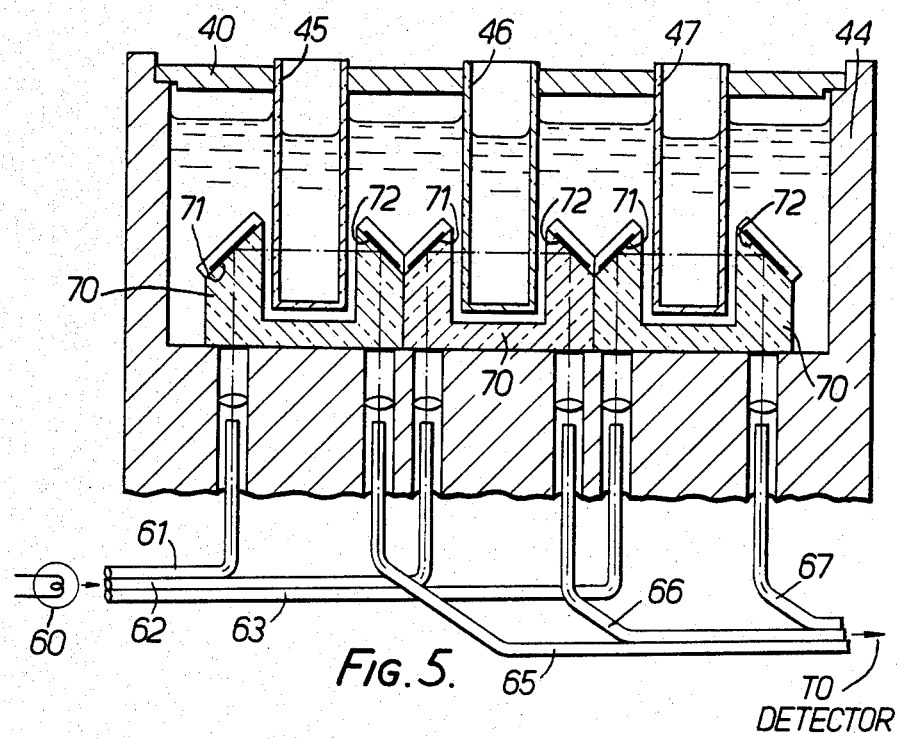
FIG. 5 is a sectional view of another embodiment of an apparatus for simultaneously measuring a plurality of samples.

FIG. 5 shows another embodiment of the simultaneous measuring apparatus in which a plurality of U-shaped prism means 70 is provided. Each prism 70 has a pair of light path conversion planes 71 and 72 on which at least two layers of light reflective and chemically resistant material are deposited.

Figure 6:
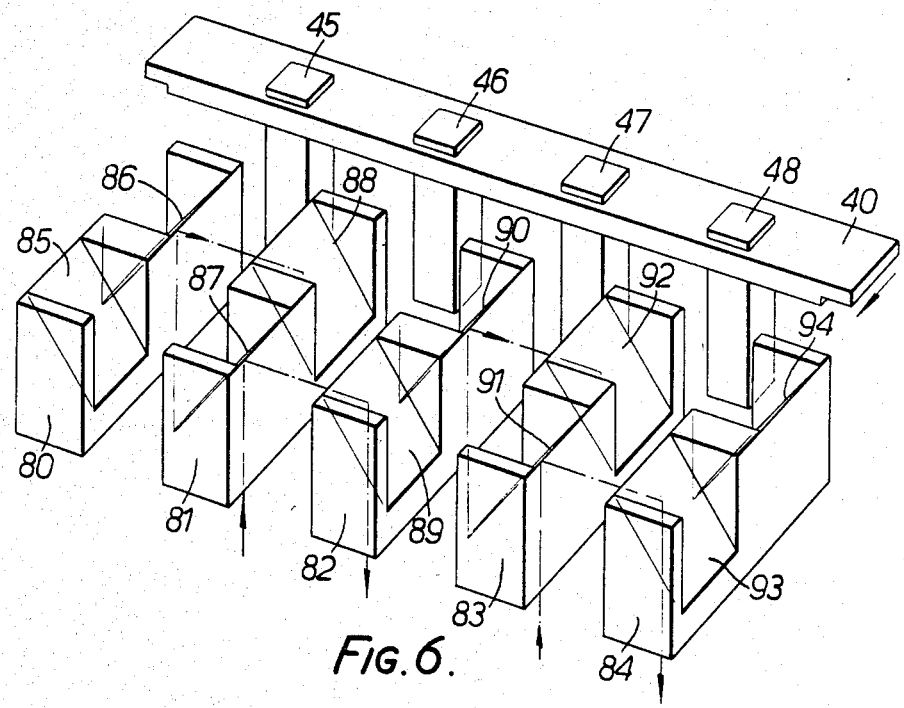
FIG. 6 is a perspective view of a further embodiment of prism means employing a staggered light path arrangement for performing simultaneous measurement of plural samples using a compact optical path.

FIG. 6 shows a plurality of staggered prisms which can perform simultaneous measurement of plural samples in a much more compact apparatus than the apparatus shown in FIG. 4. In this figure, only the prism means and the cuvette support cassette holding a plurality of sample cuvettes are shown for purposes of simplicity. Cassette 40 moves across a temperature bath unit (not shown) and moves a plurality of cuvettes 45, 46, 47 and 48 past light intensity measuring sections employing a plurality of staggered light paths defined by a plurality of specially formed prisms 80, 81, 82, 83 and 84.

Each prism includes two light path conversion planes of opposite inclination with respect to each other. Prism 80 has two light path conversion planes 85 and 86. Prism 81 has planes 87 and 88, and so on. The confronting surfaces 86 and 88 define a light measuring path and the confronting surfaces 87 and 89 of the prisms 81 and 82 define another light path staggered with respect to the path 86–88. By this staggered light path construction, simultaneous plural measurement can be performed by a compact apparatus.

What is claimed is:

1. Photometric analyzing apparatus comprising:
  temperature controlled bath unit means including at least a pair of light entrance and exit windows at the bottom portion thereof;
  light path conversion means positioned adjacent to said respective windows of said bath unit means, said light path conversion means comprising at least a first thin layer of light reflective material applied to a light path conversion surface thereof and a second thin layer of chemically resistant material covering said first layer, said light path conversion means defining a light inspection path;
  means for positioning a fluid sample within said bath unit means in said light inspection path; and
  means for transmitting a light beam through said light path conversion means to irradiate said fluid sample for photometric analysis.

2. Photometric analyzing apparatus according to claim 1 wherein said light reflective material is aluminum, and said chemically resistant material is selected from a group consisting of titanium, chlorine and silicon.

3. Photometric analyzing apparatus according to claim 1 further comprising a third thin layer of chemically resistant material covering said second thin layer of chemically resistant material.

4. Apparatus according to claim 3 wherein said second thin layer comprises a buffer layer of chlorine and said third thin layer comprises a top covering layer of titanium.

5. Apparatus according to claim 1 further comprising a glass plate adhesively fixed to cover said thin layer of chemically resistant material.

6. Photometric analyzing apparatus for simultaneously measuring plural samples comprising;

means movable along a temperature controlled bath unit for supporting a plurality of sample cuvettes partially immersed in a fluid medium contained in said bath unit;

a plurality of light path conversion means positioned in said bath unit, each including at least a light reflective layer and a chemically resistant layer thereon defining a light inspection path intersecting one of said sample cuvettes; and means transmitting a light beam through said plurality of light path conversion means to simultaneously irradiate said plurality of sample cuvettes for photometric analysis.

7. Apparatus according to claim 6 wherein each said light path conversion means has a U-shaped body.

8. Apparatus according to claim 6 wherein each of said light path conversion means includes two different angled light reflection surfaces defining a plurality of staggered light inspection paths.

* * * * *